US009429553B2

(12) United States Patent
Jaunakais et al.

(10) Patent No.: US 9,429,553 B2
(45) Date of Patent: Aug. 30, 2016

(54) PROCESSOR-BASED ANALYSIS SYSTEM AND METHOD

(71) Applicants: Lea M. Jaunakais, Rock Hill, SC (US); Andrew J. Roberts, Tega Cay, SC (US); George L. Bailey, II, York, SC (US); Michael C. McBride, Fort Mill, SC (US); John R. Wright, Rock Hill, SC (US)

(72) Inventors: Lea M. Jaunakais, Rock Hill, SC (US); Andrew J. Roberts, Tega Cay, SC (US); George L. Bailey, II, York, SC (US); Michael C. McBride, Fort Mill, SC (US); John R. Wright, Rock Hill, SC (US)

(73) Assignee: Industrial Test Systems, Inc., Rock Hill, SC (US)

( * ) Notice: Subject to any disclaimer, the term of this patent is extended or adjusted under 35 U.S.C. 154(b) by 777 days.

(21) Appl. No.: 13/651,305

(22) Filed: Oct. 12, 2012

(65) Prior Publication Data
US 2014/0107939 A1   Apr. 17, 2014

(51) Int. Cl.
*G01N 33/18* (2006.01)
*G01N 33/00* (2006.01)
*G06F 19/00* (2011.01)

(52) U.S. Cl.
CPC ............. *G01N 33/18* (2013.01); *G06F 19/709* (2013.01); *G06F 19/708* (2013.01)

(58) Field of Classification Search
CPC ........ G01N 31/00; G01N 33/18; G06F 19/00
See application file for complete search history.

(56) References Cited

U.S. PATENT DOCUMENTS

| | | | |
|---|---|---|---|
| 6,353,926 B1* | 3/2002 | Parthesarathy et al. | 717/170 |
| 7,164,132 B2* | 1/2007 | Didomenico | G01N 21/3504 250/338.5 |
| 7,333,194 B2 | 2/2008 | Jaunakais et al. | |
| 7,489,986 B1* | 2/2009 | Laflamme | A61H 33/0087 340/4.3 |
| 7,920,983 B1* | 4/2011 | Peleg | G01M 3/2807 137/1 |
| 2002/0130069 A1* | 9/2002 | Moskoff | C02F 1/008 210/85 |

(Continued)

FOREIGN PATENT DOCUMENTS

WO   WO2007053515 A1   5/2007
WO   WO2011132863   * 10/2011

(Continued)

OTHER PUBLICATIONS

Qiulan Wu, Application of GPRS Technology in water Quality Monitoring System, Sep. 19-23, 2010, IEEE, ISBN:978-1.4244-9673-0, 7-11.*

(Continued)

*Primary Examiner* — Hyun Park
*Assistant Examiner* — Mohammad Islam
(74) *Attorney, Agent, or Firm* — Timothy R. Kroboth

(57) ABSTRACT

The present invention is directed to a processor-based analysis system and method. The technology includes a water analysis computer program, which may be an app for a smart device. Beneficially, an interactive visual display device is in communication with a sensing device. Advantageously, test parameter algorithms may be updated, and use of an auxiliary product with an intended test may be validated. Benefits further include improved accuracy of test results, user customization, and storage, management and output of associated data.

25 Claims, 6 Drawing Sheets

(56) References Cited

U.S. PATENT DOCUMENTS

| | | | | |
|---|---|---|---|---|
| 2003/0154044 A1* | 8/2003 | Lundstedt | G01N 21/274 | 702/104 |
| 2003/0216949 A1* | 11/2003 | Kram | G06Q 10/02 | 705/5 |
| 2004/0130713 A1* | 7/2004 | O'Mongain | G01N 21/31 | 356/300 |
| 2004/0138840 A1 | 7/2004 | Wolfe | | |
| 2004/0197229 A1* | 10/2004 | Runyon | B01L 9/02 | 422/63 |
| 2005/0118704 A1* | 6/2005 | Malobabic | G01N 1/14 | 435/287.1 |
| 2006/0066858 A1* | 3/2006 | Jaunakais | G01N 21/0303 | 356/436 |
| 2006/0198761 A1* | 9/2006 | Tokhtuev | G01N 21/251 | 422/82.05 |
| 2007/0219728 A1 | 9/2007 | Papageorgiou et al. | | |
| 2009/0098022 A1* | 4/2009 | Tokhtuev | G01N 21/274 | 422/82.05 |
| 2009/0245603 A1* | 10/2009 | Koruga | A45D 44/00 | 382/128 |
| 2010/0105146 A1 | 4/2010 | Meeusen | | |
| 2010/0188236 A1* | 7/2010 | Biberger | G01N 33/18 | 340/603 |
| 2010/0204924 A1* | 8/2010 | Wolfe | C02F 1/008 | 702/25 |
| 2011/0053283 A1* | 3/2011 | Hood | G01N 33/14 | 436/104 |
| 2011/0093941 A1* | 4/2011 | Liu et al. | | 726/7 |
| 2011/0125412 A1* | 5/2011 | Salzer | C02F 1/008 | 702/22 |
| 2011/0304475 A1 | 12/2011 | Higgins et al. | | |
| 2011/0307203 A1 | 12/2011 | Higgins et al. | | |
| 2012/0015445 A1* | 1/2012 | Kellner | G01N 21/6428 | 436/172 |
| 2012/0057782 A1* | 3/2012 | Bick | H04M 1/72522 | 382/165 |
| 2013/0029683 A1* | 1/2013 | Kim | G01N 33/18 | 455/456.1 |
| 2013/0132165 A1* | 5/2013 | McNeill | G06Q 10/10 | 705/7.39 |
| 2013/0318461 A1* | 11/2013 | Trafton | G06F 3/0484 | 715/771 |
| 2014/0068595 A1* | 3/2014 | Belinsky | G06F 8/65 | 717/173 |

FOREIGN PATENT DOCUMENTS

| | | |
|---|---|---|
| WO | WO2012049666 A2 | 4/2012 |
| WO | WO2012131386 A1 | 10/2012 |

OTHER PUBLICATIONS

Dongling Ma, "Design and realization of water quality information management system based of GIS", 2010, IEEE,2010-k9-24.*

Pool & Spa News, Small, But Powerful, May 14, 2010, pp. 1-4.*

Z-INST 9 PREM, Plain test Pool test 9 manual, Dec. 2011, V6, pp. 1-3.*

Palintest-9 , PALINTEST Pooltest 9 Photometer manual ver. V6, Dec. 2011.*

Wu et al., Application of GPRS Technology in Water Quality Monitoring System,Sep. 2010, IEEE, pp. 7-11.*

Ma et al., Design and realization of water quality information mnagement system based of gis, 2010, IEEE.*

PCT/US2013/000230, International Search Report and Written Opinion, Jan. 16, 2014.

LaMotte Company, Insta-Link Home Pool and Spa Care, www.insta-link.com,web pp. 2, Aug. 31, 2012.

Sensorex, PH-1 pH Meter for iPhone & iPad, www.sensorex.com,web pp. 2, Aug. 19, 2012.

Kurschi, "Combining Cloud Computing and Wireless Sensor Networks", Proceedings of iiWAS2009, pp. 512-518, Dec. 14-16, 2009.

PCT/US2013/000230, Extended European Search Report, Apr. 1, 2016.

* cited by examiner

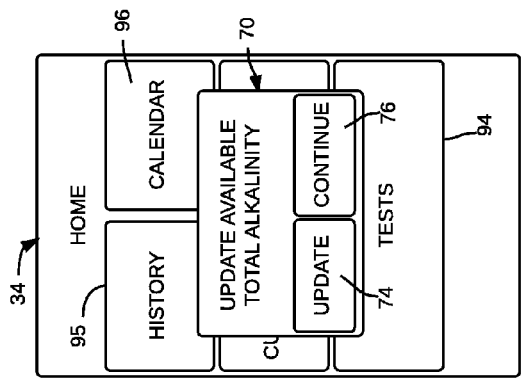
FIG. 4
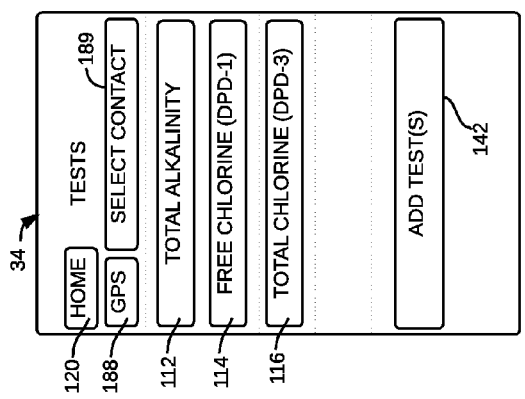
FIG. 5
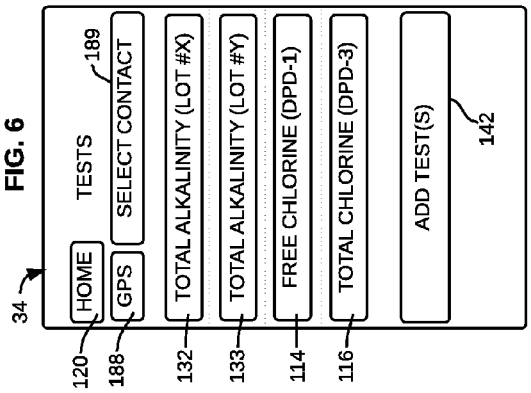
FIG. 6
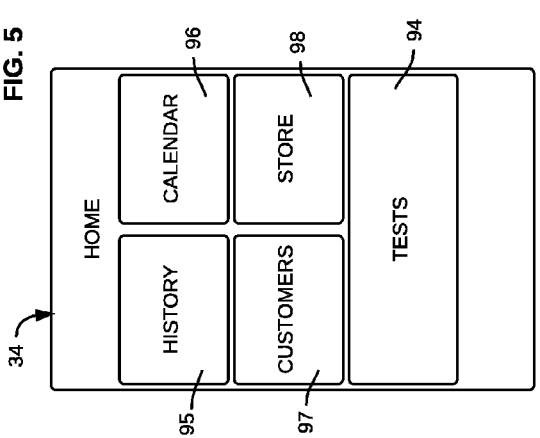
FIG. 7
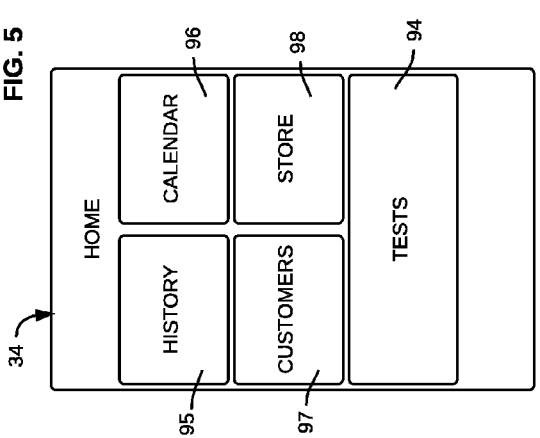
FIG. 8
FIG. 9

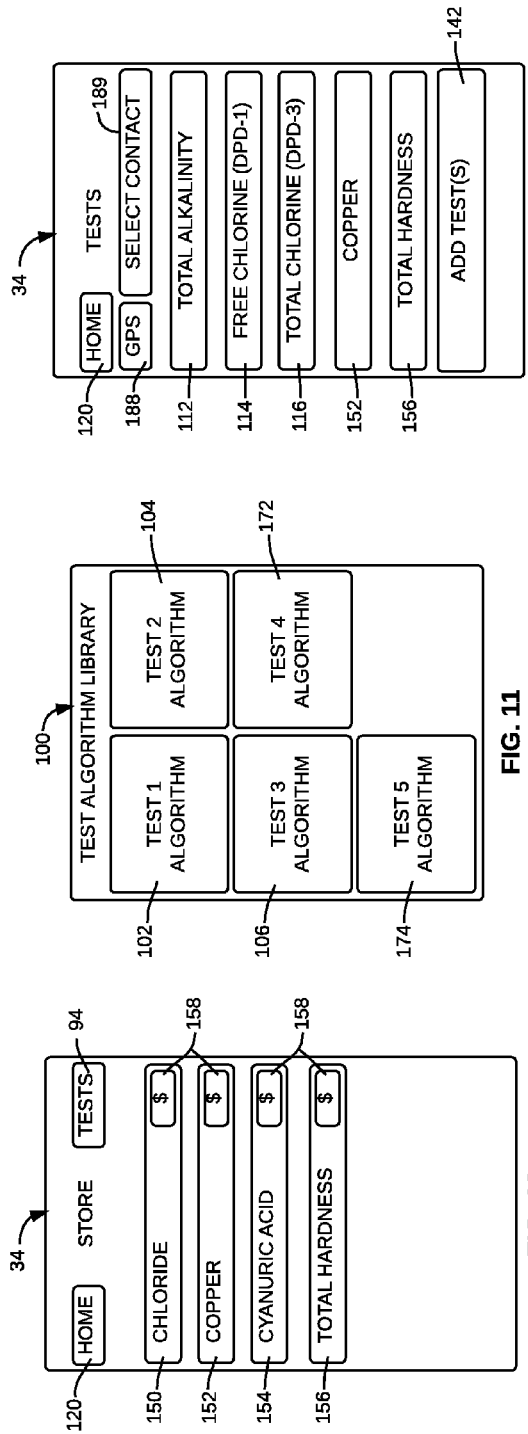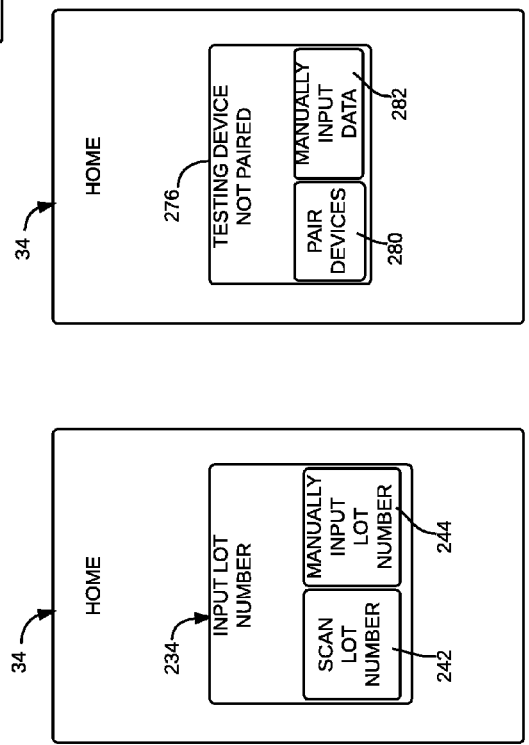

PROCESSOR-BASED ANALYSIS SYSTEM AND METHOD

FIELD OF THE INVENTION

The present invention relates to processor-based water analysis.

BACKGROUND OF THE INVENTION

In processor-based water analysis, data for a selected water parameter is typically processed using an algorithm appropriate for the selected water parameter. Illustrative of this type of analysis is U.S. Pat. No. 7,333,194 to Jaunakais et al., which at col. 10, lines 1-4, describes storage by photometric instruments of test parameter algorithms appropriate for interpreting the data obtained. This type of analytical method benefits accuracy compared to visual color matching methods.

With further reference to the Jaunakais patent, FIG. 7 is illustrative of colorimetric methods using auxiliary products. FIG. 7 further illustrates touch pads for operation of the photometric instrument, and a display for viewing operation and the test results. FIG. 7 and the description relating thereto are hereby incorporated herein by reference.

To take into account any sample temperature effect on test results, electrochemical sensing devices are commercially available that include test parameter sensors and sample temperature sensors, as well as test parameter algorithms that may be temperature variable in response to sample temperature.

Also commercially available is a pH probe and sample temperature sensor connected by wire to a smart device, which operates by sensors communicating test data to the smart device. Also commercially available is a web-hosted app for use with a smart phone, in which after a test strip has been dipped in a sample, the test strip is placed on a color reference card, and a digitized image of the test strip on the reference card is captured using a smart phone scanning function, and test results are displayed by the smart phone.

As exemplified by published U.S. Patent Application Nos. 2010/0188236 to Biberger, 2011/0304475 to Higgins et al., and 2011/0307203 to Higgins et al., remote monitoring of water quality conditions including conductivity, turbidity, pH, dissolved solids, concentrations of various metals, and concentrations of various ions, at one or more locations is also known.

Despite improvements resulting from the use of processor-based water analysis, there continues to be a need for improving the accuracy of test results and user customization.

SUMMARY OF THE INVENTION

The present invention is directed to a processor-based analysis system and method for water analysis, including water-based analysis, for example, of antifreeze coolants and diesel exhaust fluids. The inventive processor-based analysis system includes a sensing device that includes a sensor and processor in electronic communication with the sensor for obtaining raw data for a selected analysis parameter. The inventive analysis system also includes an interactive visual display device that includes a visual display and a processor in electronic communication with the visual display.

Running on the processor of the interactive visual display device is a water analysis computer program, which may be an app for a smart device. The processor is in communication with a database that includes a plurality of test parameter algorithms from which a test parameter algorithm may be selectable for a selected analysis parameter. The processor is beneficially in communication with the sensing device for communicating a selected analysis parameter to the sensing device, and for receiving raw data from the sensing device. The processor communicates the raw data to the selected test parameter algorithm, and receives test result data from the selected test parameter algorithm. Thereafter, the processor conveniently communicates the test result data for display and storage. A test parameter algorithm library conveniently includes the plurality of test parameter algorithms from which an available test parameter algorithm is selectable.

Beneficially, the inventive analysis system further includes means for communication for customizing or updating the test parameter algorithms. The test parameter algorithm library may conveniently include a plurality of unavailable test parameter algorithms available for purchase. Conveniently, a test parameter algorithm store accessible by the means for communication may include a plurality of test parameter algorithms available for purchase. Beneficially, the visual display of the interactive visual display device may display alerts that include alerts to update the computer program or one or more test parameter algorithms in the test parameter algorithm library.

Commercial auxiliary analysis products or containers for auxiliary analysis products are marked with identifying product information. Beneficially, when intended for use with auxiliary analysis products, test parameter algorithms may be associated with identifying product data. Advantageously, the inventive analysis system includes an image capture device for scanning identifying product data associated with auxiliary products. Beneficially, the processor of the interactive visual display device compares identifying product data of auxiliary products with identifying product data associated with the selected test parameter algorithm. Advantageously, identifying product data of auxiliary products may be stored in the database, and test result data may be associated with identifying product data of auxiliary products.

The sensing device may be a photometric instrument. When the sensing device is a photometric instrument and includes a temperature sensor in addition to the sensor for obtaining raw data for a selected analysis parameter, it is advantageous for test parameter algorithms to be temperature variable. The sensing device may be a hand held device. When the sensing device is a hand held device, the sensing device may conveniently further include manual input means such as a touchpad, and a visual display in electronic communication with the sensing device processor. The sensing device may include a well for capturing a sample upon immersion of the well in a water source or upon flow of water into the well.

Advantageously, the inventive analysis system may include a global positioning system, and a time/date device in electronic communication with the processor of the interactive visual display device. As a result, test result data may be associated with a specific location, and in addition may be associated with time/data data.

Beneficially, the inventive analysis system is capable of communication with a cloud that includes data repositories for sharing data, such as social media data repositories and crowd sourcing data repositories, and that includes secure data repositories. The database may be in a data repository in the cloud.

Also provided is a processor-based analysis method. The inventive method advantageously includes in one aspect, updating a test parameter algorithm, selecting a water parameter for analysis, selecting an updated test parameter algorithm for analysis of the selected water parameter, communicating the selected water parameter from an interactive visual display device to a sensing device, communicating raw data from the sensing device to the interactive visual display device, communicating the raw data to the updated test parameter algorithm, and receiving test result data from the updated test parameter algorithm.

The inventive method beneficially includes in another aspect, customizing a test parameter algorithm library by selection of test parameter algorithms available for purchase, selecting a water parameter for analysis, selecting a test parameter algorithm from a plurality of available test parameter algorithms in the library, communicating the selected water parameter from an interactive visual display device to a sensing device, communicating raw data from the sensing device to the interactive visual display device, communicating the raw data to the selected test parameter algorithm, and receiving test result data from the selected test parameter algorithm.

The inventive method advantageously includes in yet another aspect, selecting a water parameter for analysis, selecting a test parameter algorithm associated with identifying product data, comparing identifying product data associated with an auxiliary product with identifying product data associated with the selected test parameter algorithm, communicating the selected water parameter from an interactive visual display device to a sensing device, communicating raw data from the sensing device to the interactive visual display device, communicating the raw data to the selected test parameter algorithm, and receiving test result data from the selected test parameter algorithm. Beneficially, the method further comprises scanning the identifying product data associated with the auxiliary product.

Benefits of the inventive technology include updating a downloaded water analysis computer program, which may be an app for a smart device, and updating test parameter algorithms, as well as user customization. Benefits further include improved accuracy of results, as well as validating use of a particular auxiliary product with an intended test.

Additional advantages and beneficial features of the present invention are set forth in the drawing and detailed description, and in part will become apparent to those skilled in the art upon examination of the drawing and detailed description or may be learned by practice of the invention. As will be realized, this invention is capable of other and different embodiments than those described, and its several details are capable of modification in various respects, such as changes in the order of the method steps, all without departing from the invention. Furthermore, the drawing and the detailed description are to be regarded as illustrative in nature, and not as restrictive.

BRIEF DESCRIPTION OF THE DRAWING

Reference now is made to the accompanying drawing which forms a part of the specification of the present invention.

FIGS. 4, 7, and 11 are schematic diagrams relating to a test parameter algorithm library;

FIGS. 5, 6, 8-10 and 12-14 depict illustrative visual displays; and

DETAILED DESCRIPTION OF THE INVENTION

The present invention may be beneficially used by, for example, home owners, pool or spa owners, pool stores, pool or spa servicemen, municipalities, and technicians for testing water quality. Industrial uses include, but are not limited to, analyzing cooling tower water or boiler water, waste water, antifreeze/coolants, and diesel exhaust fluids for chloride, pH and other analytes.

Advantageously, the present invention includes features for updating a water analysis computer program, which may be a downloaded app for a smart device, and updating test parameter algorithms, and for customizing a water analysis app. The present invention beneficially also includes the feature of comparing identifying product data associated with an auxiliary product with identifying product data associated with a test parameter algorithm and determining whether an auxiliary product may be used for an intended test. In addition, the present invention advantageously includes features for communicating raw data from a sensing device to an interactive visual display device for processing of raw data by a selected test parameter algorithm, and for communicating data to data repositories for, for example, storage, management or sharing of data, and for communicating data to social media and crowd sourcing data repositories.

The invention is particularly useful when water analysis involves the use of an auxiliary product. Useful auxiliary products are illustrated by test strips, Powder Pillows, and auxiliary solid or liquid test chemicals. Commercial auxiliary products or containers for commercial auxiliary products, are marked with identifying product information such as product name, lot number and expiration date. By the term "identifying product data" is meant, for purposes of this description, data unique to a lot or batch of product.

Figure 1:
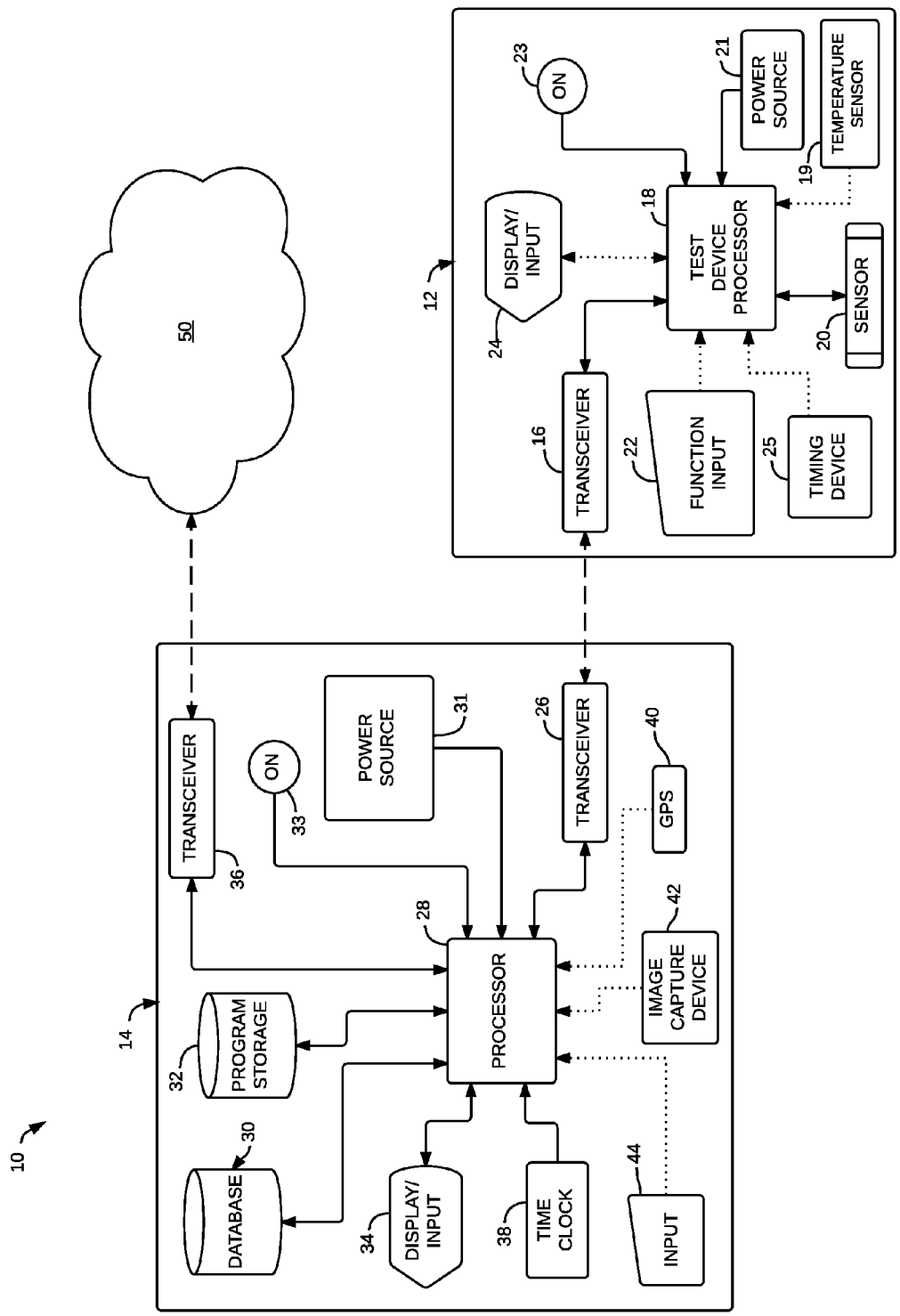
FIG. 1 is an illustrative schematic diagram that provides an overview of components of an embodiment of the inventive processor-based analysis system.

Referring to an inventive embodiment illustrated by FIG. 1, a processor-based analysis system 10 in accordance with the present invention, beneficially includes an analytical sensing device 12 and an interactive visual display device 14. The term "interactive visual display device" refers to a visual display device that a user may interact with by means of an input device. The input device may be, for example, a touchscreen of the visual display device, a touchpad, a mouse, a trackball, or a keyboard. Examples of interactive visual display devices include smart devices such as smart phones, tablet computers, personal data assistants (PDAs), and also include notebooks, laptop computers and computers with stand-alone monitors.

As illustrated, sensing device 12 includes a transceiver 16 in electronic communication with a processor 18 and a sensor 20 for obtaining data for a selected analysis parameter, and transmitting/receiving data or information via any suitable mode of communication. A computer program appropriate for sensing device operation runs on processor 18.

Sensing device 12 conveniently includes in electronic communication with processor 18, a power source 21 and "on" button 23 for powering the device. Sensing device 12 may beneficially be a portable, hand held device.

As illustrated, interactive visual display device 14 includes a transceiver 26 in electronic communication with a processor 28, which is advantageously in electronic communication with a database 30, program storage 32, a display/input 34, and a time clock 38. The database beneficially includes a test algorithm library 100, illustratively depicted by FIG. 4, and plurality of files each of which is advantageously assigned a unique record number.

Database 30 may conveniently include a plurality of customer records, each including a plurality of test history files. Each customer record may additionally include alphanumeric information pertaining to a customer such as a customer's name, address, and home and cell telephone numbers. Conveniently, digitized images of test sites may be captured by an image capture device 42, and other information may be scanned into customer records by image capture device 42. Customer information should be confirmed to be current, and if not current, may be updated, and additional alphanumeric information may be added to a customer record, such as alphanumeric information identifying the individual performing the test.

A database history file for a selected water parameter test may include information pertaining to the test such as customer name, test location, the test selected, the auxiliary product name, identifying product data, time/date data, raw test data, and test results.

Visual display 34 may be part of the interactive visual display device, or may be a peripheral component as in the case of a desk top computer. The visual display may be any type of visual display, such as a CRT monitor, LCD screen and LED screen, appropriate for a particular interactive visual display device, and as previously described, may be a touchscreen or touchpad visual display. For purposes of the following description, display 34 is usually referred to as a touchscreen.

As illustrated, device 14 conveniently includes in electronic communication with processor 28, a power source 31 and "on" button 33 for powering the device, may advantageously include a transceiver 36 for communication with a cloud 50, generally considered a network of offsite computer resources, and optionally (as indicated by dotted lines) includes global positioning system (GPS) input 40, image capture device 42, and an input 44. Transceiver 36 may also function to provide location services. GPS, image capture, and input features may be peripheral components. An image capture feature may beneficially function as a camera or scanner for capture of image data. Display 34 may provide only for visual display, in which case an input feature such as input 44, may be advantageous for manual input of information.

Conveniently, communication between devices 12,14 may be provided by transceivers 16,26. By the term "transceiver" is meant, for purposes of this description, a device capable of transmitting data or information via any suitable wireless mode of communication. Useful transceivers may be internal as illustrated, or may be peripheral devices. Useful transceivers include RF and IR transceivers. RF transceivers are illustrated by Bluetooth® transceivers, wi-fi transceivers and cellular transceivers. Peripheral transceivers, some of which are referred to as dongles, may be RF or IR transceivers.

Communication with cloud 50 may be provided by transceiver 26, in which case transceiver 36 may be optional. Whether transceiver 36 is optional can generally be considered to depend upon the mode of communication between devices 12,14. For example, when devices 12,14 communicate via Bluetooth® transceivers or IR transceivers, transceiver 36 may conveniently be, for example, a wi-fi or cellular transceiver so as to provide for communication with cloud 50. However, when devices 12,14 communicate via, for example, wi-fi or cellular transceivers, transceiver 26 may be used for communication with both sensing device 12 and cloud 50.

As indicated by FIG. 1, database information may be stored using electronic information storage of cloud 50.

By the term "mode of communication" is meant, for purposes of this description, any suitable wireless technology for communicating between two or more devices such as devices 12,14, and cloud 50. The mode of communication may be achieved or carried out through any suitable medium, as well as any protocols including internet protocol or other data transmission protocol as may be advantageously used. Illustrative modes of communication may include wi-fi, network, digital living network alliance (DLNA), near field communication (NFC) and Bluetooth® protocols, and IR medium and RF medium.

With continued reference to sensing device 12, a useful sensor may obtain data by photometry, electrochemistry or nephelometry. Useful photometric sensors include colorimetric and turbidimetric sensors. Photometric analysis typically involves the use of an auxiliary product. Useful electrochemical sensors may, for example, analyze pH, total dissolved solids (TDS), and oxidation/reduction potential (ORP).

For colorimetric measurement, photometric instruments are widely used, and are illustrated by U.S. Pat. No. 7,333, 194 to Jaunakais et al. Illustrative photometric instruments are filter photometers, photometers without filters, and spectrophotometers. A beneficial photometric instrument may be waterproof, and may include a cell chamber or well for holding the sample to be analyzed, and as sensor components, a suitable light source and light detector. With respect to further details as to these and related photometric sensor features, FIG. 10 and the description at col. 9, lines 34-46 and 52-67, of the '194 patent are hereby incorporated by reference.

By the term "waterproof" is meant, for purposes of this description, with respect to sensing device 12, impervious to water, and is to be distinguished from water-resistant. The imperviousness of a waterproof sensing device beneficially protects function-critical components, including but not limited to, electronic and power components, from contact with water. A waterproof sensing device may be at least partially immersed in a body of water or may be contacted with a flow of water, for data collection or for sample collection.

With continued reference to FIG. 1, the location of sensor 20 is appropriate for data or sample collection. In the case of a partially or fully immersible photometric instrument, sensor 20 and a sample well or cell chamber, if present, may conveniently be located near or at an end of the sensing device.

As illustrated by FIG. 1, sensing device 12 may optionally (as illustrated by dotted lines) include in electronic communication with processor 18, a temperature sensor 19, one or more touchpads 22 (one shown as "FUNCTION INPUT") for functions including zeroing (or blanking) water samples and initiating countdown timing of tests, and a display/input 24 for information display such as "device paired", the test selected, test countdown timing, and test results, and for controlling one or more functions that may be controlled by manual function input 22. In addition, sensing device 12 may optionally include a timing device 25 for test countdown timing, and for automatically turning sensing device 12 off after a predetermined period of device inactivity. Although the touchpad and display functions may be controlled or carried out by interactive visual display device 14, for a hand held device manual function input 22 is convenient for functions including zeroing water samples and initiating countdown timing of tests, and display 24 is convenient for information display.

With reference to FIG. 4 and test algorithm library 100 of database 30, useful test parameter algorithms may be temperature variable. Thus, when sensing device 12 is a photometric instrument and beneficially includes temperature sensor 19, sample temperatures may be communicated to processor 28 for the processor to modify the test parameter algorithms so as to be appropriate for sample temperatures.

With continued reference to FIG. 1 and to device 14, optional image capture device 42 may beneficially function as a scanner for capturing identifying product data encoded, for example, as QR codes, dot matrix codes or barcodes. To this end, when the inventive processor-based analysis system and method include or use an auxiliary product, identifying product data may be printed in encoded form on, or on an identification tag affixed to, the auxiliary product. In this way, identifying product data may be captured by scanning encoded data, and stored, and may advantageously be used, for example, for validating use of a particular product with an intended test, and for updating a database file with identifying product data, thereby associating the tests results with the auxiliary product used.

Image capture device 42 is beneficially in electronic communication with processor 28 for communicating identifying product data captured by image capture device 42 to processor 28 for evaluation by the processor as later described, and in addition with database 30 for storage of identifying product data and for updating database files with identifying product data.

Test Parameter Algorithm Update Feature

Figure 2:
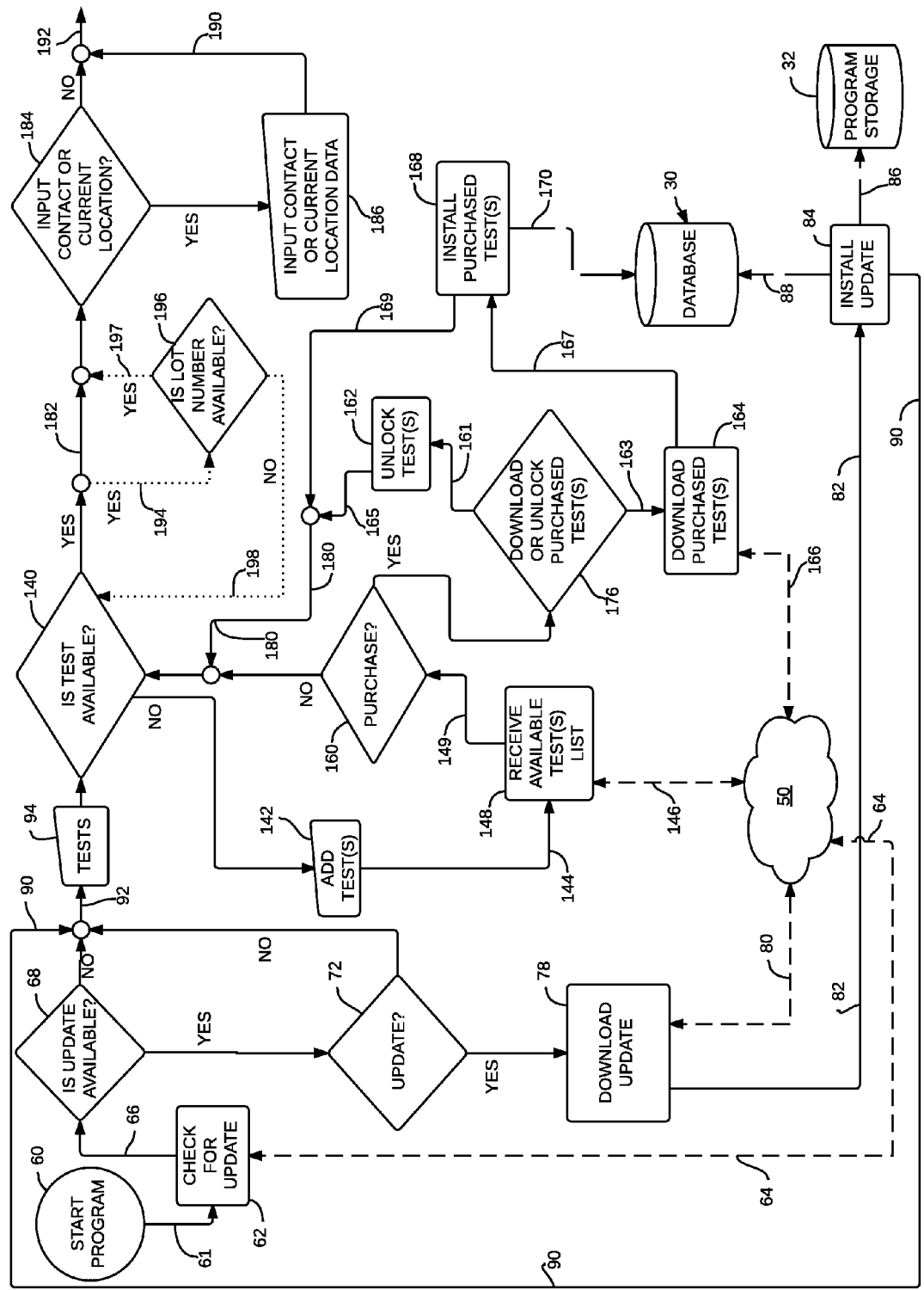
FIGS. 2 and 3 depict an illustrative flow diagram.

With reference to the simplified flow chart of FIG. 2, and as depicted by "START PROGRAM" button 60, a user begins by selecting the water analysis computer program or app for use. Upon start up of the water analysis program, the program, as depicted by line 61 and "CHECK FOR UPDATE" box 62 and two-way line 64, queries cloud 50 via transceiver 36 of device 14, for any update to the water analysis program (or app). As depicted by line 66 and "IS UPDATE AVAILABLE?" decision box 68 (see FIG. 2), the return of the query is communicated to processor 28, which determines whether an update is available. If "yes", a user may be informed by means of touchscreen 34 that an update is available. Availability of an update is illustrated by "UPDATE AVAILABLE" information box 70 of FIG. 6. As depicted by "UPDATE?" decision box 72 (see FIG. 2), a user may choose to update the program as indicated by a "yes" decision line, or choose not to update the program as indicated by a "no" decision line. As depicted by FIG. 6, selecting "UPDATE", indicated by line 74, on touchscreen 34 corresponds to a "yes" decision, and selecting "CONTINUE", indicated by line 76, on touchscreen 34 corresponds to "no".

With continued reference to FIG. 2, in response to selecting "UPDATE?", indicated by the "yes" decision line, transceiver 36 provides for communication with cloud 50 for downloading an update, as depicted by "DOWNLOAD UPDATE" box 78 and two-way line 80, and thereafter, as depicted by line 82, "INSTALL UPDATE" box 84 and line 86, when an update is a program update, the update is installed in program storage 32.

As depicted by line 88 from "INSTALL UPDATE" box 84, when the update includes a test parameter algorithm update, the test parameter algorithm update is installed in database 30 and specifically in test algorithm library 100 (see FIG. 7) of database 30, and other update code may be installed in program storage 32.

With continued reference to FIG. 2, if, as indicated by a "no" response of processor 28 to the query "IS UPDATE AVAILABLE?", an update is not available, or if the response of a user to "UPDATE?" is "no", or if, as indicated by line 90 from "INSTALL UPDATE" box 84, an update has been installed, then as depicted by line 92, device 14 may indicate to a user by means of touchscreen 34, a menu of choices as illustrated by FIG. 8, which includes "TESTS", indicated by line 94.

Referring now to FIG. 4, database 30 includes a test algorithm library 100. As depicted by FIG. 4, the test algorithm library may include three algorithms for testing three parameters: an algorithm for test 1 (depicted by "TEST 1 ALGORITHM" box 102), an algorithm for test 2 (depicted by "TEST 2 ALGORITHM" box 104), and an algorithm for test 3 (depicted by "TEST 3 ALGORITHM" box 106). Beneficially, each test parameter algorithm is in association with unique product identifying data, which for example, may be one or more product lot numbers.

A corresponding menu of available tests conveniently viewable by selecting "TESTS", indicated by line 94, on touchscreen 34 (shown in FIGS. 2 and 8), is illustrated by FIG. 5. As depicted by FIG. 5, these tests are illustrated by TOTAL ALKALINITY, indicated by line 112, FREE CHLORINE (DPD-1), indicated by line 114, and TOTAL CHLORINE (DPD-3), indicated by line 116. By selecting "HOME", indicated by line 120, a "HOME" page, as illustrated by FIG. 8, is displayed.

After downloading an update that includes a test parameter algorithm update and identifying product data, an updated test algorithm for, for example, test 1 may be added to test algorithm library 100 associated with identifying product data such as one or more lot numbers, and the algorithm for test 1 (depicted by "TEST 1 ALGORITHM" box 102) may be associated by the update with identifying product data such as one or more other lot numbers, or deleted, as appropriate. As depicted by FIG. 7, test algorithm library 100 may now include four algorithms: an updated algorithm for test 1 (depicted by "TEST 1 ALGORITHM LOT X" box 122), the previous algorithm for test 1 (depicted by "TEST 1 ALGORITHM LOT Y" box 123), the algorithm for test 2 (depicted by "TEST 2 ALGORITHM" box 104), and the algorithm for test 3 (depicted by "TEST 3 ALGORITHM" box 106).

A corresponding menu of available tests conveniently viewable by selecting "TESTS" 94 (shown in FIGS. 2 and 8) on touchscreen 34, is illustrated by FIG. 9. As depicted by FIG. 9, these tests are illustrated by TOTAL ALKALINITY (LOT #X), indicated by line 132, TOTAL ALKALINITY (LOT #Y), indicated by line 133, FREE CHLORINE (DPD-1), indicated by line 114, and TOTAL CHLORINE (DPD-3), indicated by line 116.

Customizing Feature

Referring again to FIG. 2, as indicated by "IS TEST AVAILABLE?" decision box 140, if the menu of available tests does not include a test that a user wants to run, then, as indicated by a "no" decision line, a user may select "ADD TEST(S)", indicated by line 142 (also shown in FIGS. 5 and 9), on touchscreen 34.

With continued reference to FIG. 2, if a user selects "ADD TEST(S)", transceiver 36 of device 14 may provide, as depicted by lines 144 and 146, for communication with a test algorithm store in cloud 50, as a result of which, as depicted by "RECEIVE AVAILABLE TEST(S) LISTS" box 148, a list of available tests may be received. As depicted by FIG. 10, these tests are illustrated by CHLORIDE, indicated by line 150, COPPER, indicated by line 152, CYANURIC ACID, indicated by line 154, and TOTAL HARDNESS, indicated by line 156. As depicted by "$" symbols 158, each test may be purchased by selecting the appropriate "$" symbol on touchscreen 34.

With continued reference to FIG. 2, as depicted by "PURCHASE?" decision box 160 and referring again to FIG. 10, a user may choose to purchase one or more additional tests, as indicated by a "yes" decision line, or not to purchase any additional tests, as indicated by a "no" decision line. In response to "yes", "DOWNLOAD OR UPLOAD PURCHASED TEST(S)" decision box 176 conveniently provides two choices. As depicted by line 162 and "UNLOCK TEST(S)" box 162, test parameter algorithms downloaded with the water analysis program (or app) but unavailable for use, are "unlocked", that is, become available for use. As depicted by line 163, "DOWNLOAD PURCHASED TEST(S)" box 164, and line 166, transceiver 36 provides for communication with a test algorithm store in cloud 50 for downloading, one or more purchased test parameter algorithms from the test algorithm store. Thereafter, as depicted by line 167, "INSTALL PURCHASED TEST(S)" box 168 and line 170, one or more purchased test parameter algorithms is installed in test algorithm library 100 of database 30. As depicted, a line 165 from "UNLOCK TEST(S)" box 162, and a line 169 from "INSTALL PURCHASED TEST(S)" box 168 conveniently junction, and a line 180 junctions the "no" decision line from "PURCHASE" decision box 160.

As depicted by FIG. 11, test algorithm library 100 may now include five algorithms: the algorithm for test 1 (depicted by "TEST 1 ALGORITHM" box 102), the algorithm for test 2 (depicted by "TEST 2 ALGORITHM" box 104), the algorithm for test 3 (depicted by "TEST 3 ALGORITHM" box 106), an algorithm for test 4 (depicted by "TEST 4 ALGORITHM" box 172), and an algorithm for test 5 (depicted by "TEST 5 ALGORITHM" box 174).

A corresponding menu of available tests conveniently viewable by selecting "TESTS" (shown in FIGS. 2 and 8) on touchscreen 34, is illustrated by FIG. 12. As depicted by FIG. 12, these tests are illustrated by TOTAL ALKALINITY, indicated by line 112, FREE CHLORINE (DPD-1), indicated by line 114, TOTAL CHLORINE (DPD-3), indicated by line 116, COPPER, indicated by line 152, and TOTAL HARDNESS, indicated by line 156. Thus, referring again to FIG. 11, by way of illustration, TEST 1 ALGORITHM may correspond to the TOTAL ALKALINITY test, indicated by line 112, TEST 2 ALGORITHM may correspond to the FREE CHLORINE (DPD-1) test, indicated by line 114, TEST 3 ALGORITHM may correspond to the TOTAL CHLORINE (DPD-3) test, indicated by line 116, TEST 4 ALGORITHM may correspond to the COPPER test, indicated by line 152, and TEST 5 ALGORITHM may correspond to the TOTAL HARDNESS test, indicated by line 156.

With continued reference to FIG. 2, if the response to "PURCHASE?" is "no", or if, as indicated by line 180, previously unavailable test parameter algorithms have been unlocked or purchased test parameter algorithms have been installed, or if the response to "IS TEST AVAILABLE?" is "yes" (indicated by line 182), then as depicted by "INPUT CONTACT OR CURRENT LOCATION?" decision box 184, a "yes" response to "INPUT CONTACT OR CURRENT LOCATION?" provides alternatives depicted by "INPUT CONTACT OR CURRENT LOCATION" box 186. Referring now to FIG. 9, selecting "GPS" (indicated by 188) on touchscreen 34 inputs current location data, or selecting "SELECT CONTACT" (indicated by 189) on touchscreen 34 provides for inputting customer information data including address information. A "no" response to "INPUT CONTACT OR CURRENT LOCATION?" decision box 184, and line 190 from "INPUT CONTACT OR CURRENT LOCATION" box 186 lead via line 192 to "SELECT TEST" (indicated by 200 in FIG. 3).

Figure 15:
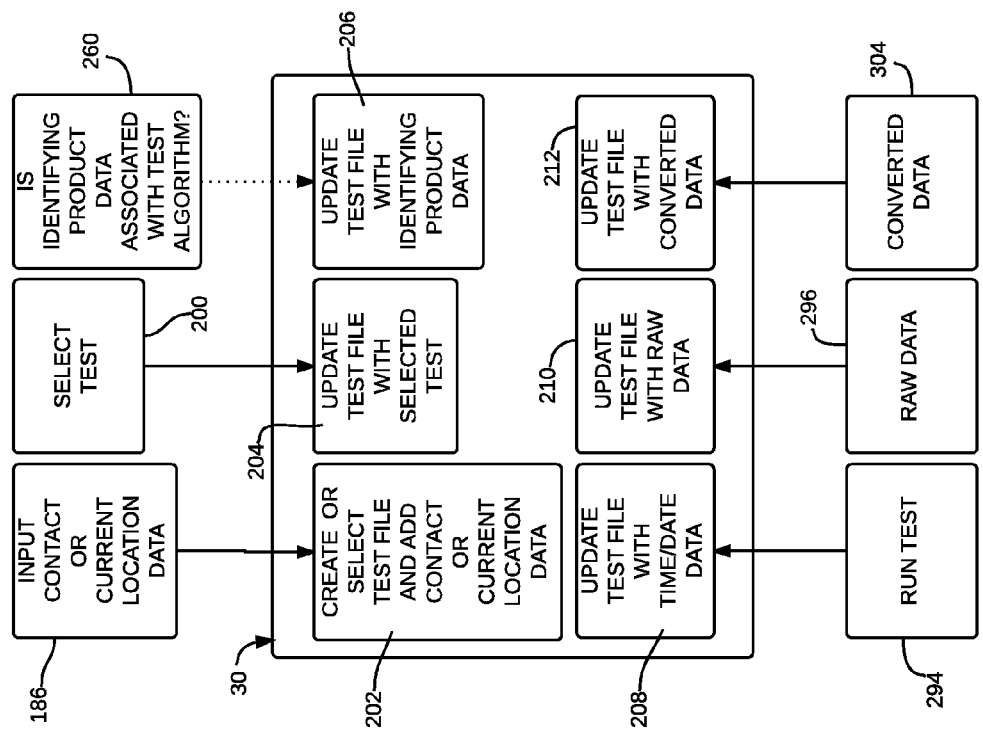

Current location data or customer history data are conveniently stored in database 30, and as depicted by box 202 of FIG. 15, a customer/location test history file relating to the current location or customer information data may be selected, or a customer/location test history file may be created for the current location data or customer information data.

As exemplified by FIG. 9, when the inventive water analysis system and method include an auxiliary product, a menu of available tests may inform a user whether a test that corresponds to identifying product data for the auxiliary product, is available. As illustrated by FIG. 9, identifying product data may be the product lot number, and the test menu may inform a user that a TOTAL ALKALINITY test is available for LOT #X, and that another TOTAL ALKALINITY test is available for LOT #Y.

Visual Comparison of Identifying Data

With reference again to FIG. 2, in a first variation, which is indicated by dotted lines that include a "yes" decision line 194, which leads to "IS LOT NUMBER AVAILABLE?" decision box 196, a user may visually compare identifying product data such as a lot number, with the menu of available tests to determine whether a test that corresponds to the identifying product data is available. Thus, for example and referring again to FIG. 9, if the lot number of a TOTAL ALKALINITY product corresponds to LOT #X or to LOT #Y of the TOTAL ALKALINITY tests, a "yes" response, shown by dotted line 197, is appropriate. However, if in this illustration, the lot number of a TOTAL ALKALINITY product does not correspond to LOT #X or to LOT #Y of the TOTAL ALKALINITY tests, a "no" response is appropriate. In such case, to carry out a TOTAL ALKALINITY test, a user should purchase a TOTAL ALKALINITY product having corresponding identifying product data. As indicated by dotted line 198, a "no" response returns a user to a menu of available choices as exemplified by FIG. 9.

The term "identifying product data" has been previously defined. Accordingly, the query "IS LOT NUMBER AVAILABLE?" in decision box 196 is merely illustrative, and should be understood as broadly relating to comparison of any product identifying data with product identifying data associated with particular tests.

Identifying Data Validation Feature

Figure 3:
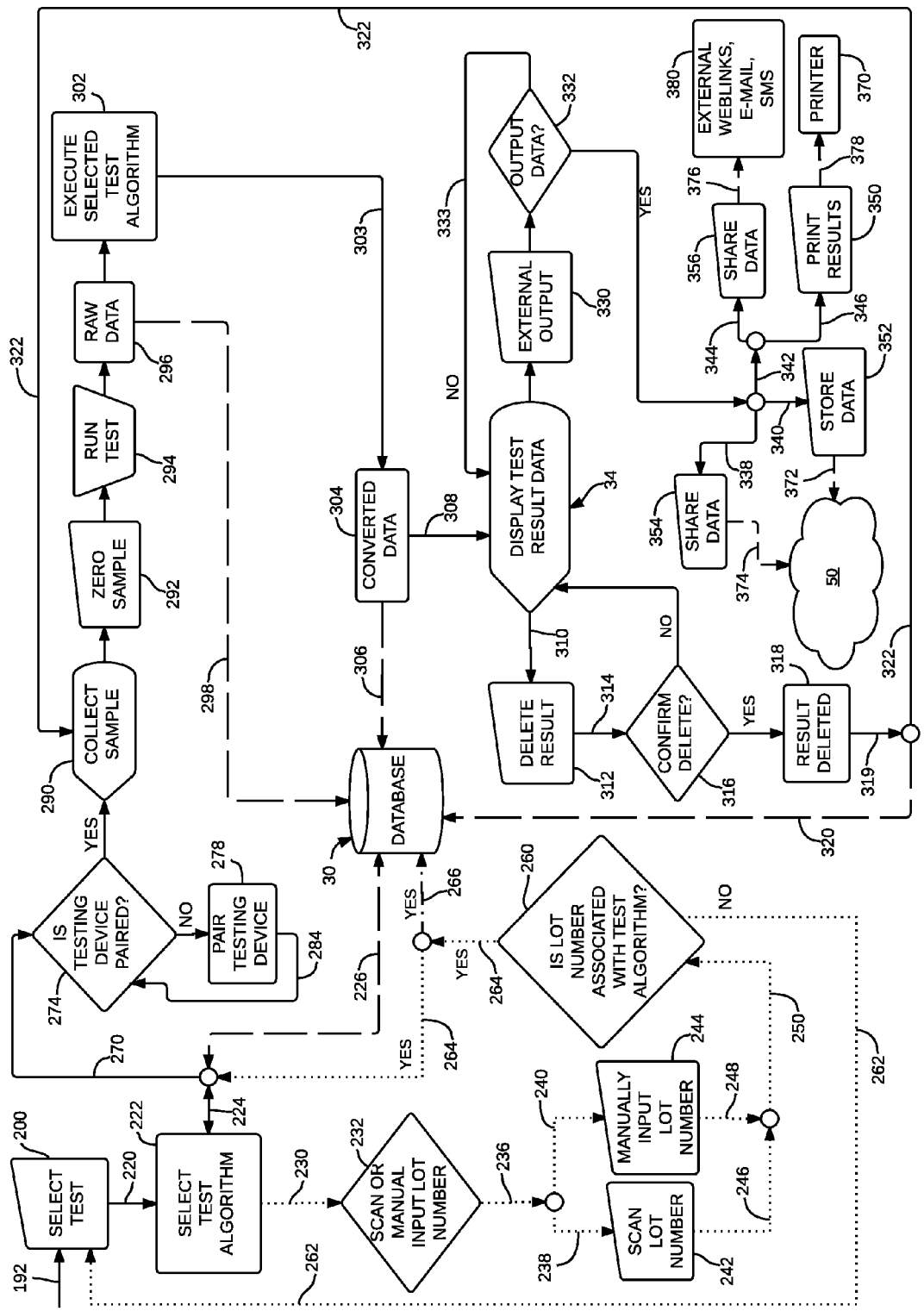

A progression from viewing a menu of available tests up to selecting a water parameter for testing has been described. With reference to FIG. 3, selecting a water parameter for testing conveniently results in a test algorithm being selected that corresponds to the water parameter selected for testing. More specifically, as depicted, a line 220 from "SELECT TEST" (indicated by 200), leads to "SELECT TEST ALGORITHM" box 222, which is illustrated as communicating by two-way lines 224 and 226 with database 30.

By way of example, referring to the menu of available tests illustrated by FIG. 12, choosing "TOTAL ALKALIN- ITY", indicated by line 112, results, as previously described, in the TOTAL ALKALINITY algorithm, indicated by box 102 in FIG. 11, being selected. Similarly, choosing "COPPER", indicated by line 152, results, as previously described, in the COPPER algorithm, indicated by box 172 in FIG. 11, being selected.

In addition, as depicted by box 204 of FIG. 15, selecting a water parameter for testing may result in the selected test being stored in database 30, and a test history file in the database being updated with the selected test. However, as a result of a "no" response to the query "INPUT CURRENT OR CONTACT LOCATION?", a test history file may be created by selecting "SELECT TEST", and the selected test stored in database 30, and added to the test history file.

With continued reference to FIG. 3, in a second variation, which is indicated by dotted lines that include line 230, processor 28 beneficially compares identifying product data with identifying product data associated with the selected test parameter algorithm. As depicted by "SCAN OR MANUAL INPUT LOT NUMBER" decision box 232, and the selection "INPUT LOT NUMBER" (indicated by line 234 in FIG. 13), a user may choose, as depicted by lines 236, 238 and 240, to scan or manually input identifying product data such as a product lot number. As previously described, image capture device 42 may be beneficially used to capture identifying product data, particularly by scanning encoded identifying product data.

Referring to FIGS. 3 and 13, as a result of selecting "SCAN LOT NUMBER" (indicated by line 242) or "MANUALLY INPUT LOT NUMBER" (indicated by line 244), identifying product information may advantageously be communicated to processor 28, as depicted by lines 246, 248 and 250.

With continued reference to FIG. 3, as depicted by "IS LOT NUMBER ASSOCIATED WITH TEST ALGORITHM" decision box 260, processor 28 compares identifying product data with the identifying product data associated with the selected test algorithm. If the result of the comparison is "no", then as indicated by "no" decision line 262, a user may select a different test from the menu of available tests. If the result of the comparison is "yes", then as depicted by lines 264, 266, and in addition by box 206 of FIG. 15, advantageously, the identifying product data may be advantageously stored in database 30, and a test history file may be updated with the identifying product data, thereby associating tests results with the auxiliary product used.

Running A Test

With continued reference to FIG. 3, regardless whether the second variation is used or not, as depicted by the combination of lines 224 and 270, or the combination of lines 264 and 270, and "IS TESTING DEVICE PAIRED?" decision box 274, the water analysis program (or app) may determine whether or not device 14 is paired with sensing device 12. If the response to the query is "no", then referring to FIG. 14, a user may be informed by "TESTING DEVICE NOT PAIRED" information box 276 of display 34 that device 14 is not paired with sensing device 12. As depicted by "PAIR TESTING DEVICE" box 278, and by a displayed selection "PAIR DEVICES", indicated by a line 280 of FIG. 14, an appropriate action is to pair devices 12,14. Pairing devices 12,14 results, as depicted by output line 284 from "PAIR TESTING DEVICE" box 278, in the water analysis program re-determining whether or not device 14 is paired with sensing device 12. A "yes" response to the query may result in a user being informed by display 34 that devices 12,14 are paired.

With reference again to "TESTING DEVICE NOT PAIRED" information box 276 (shown in FIG. 14), a displayed selection "MANUALLY INPUT DATA", indicated by a line 282, advantageously allows a user to manually input data obtained, for example, by having used a device other than sensing device 12, into database 30.

In any event with continued reference to FIG. 3, now that a test has been selected and devices 12,14 are paired, a user may, in the case of a photometric determination that involves collecting a sample, collect the sample, as conveniently informed by a displayed "COLLECT SAMPLE" instruction, indicated by line 290. Thereafter, a user may select "ZERO SAMPLE", as indicated by line 292, to zero the sample. As previously described, when sensing device 12 is a hand held device, manual function input 22 may be convenient for zeroing a sample. Likewise, display/input 24 may be convenient for observing when, for example, "0.00" is displayed.

With continued reference to FIG. 3, thereafter, as depicted by the "RUN TEST" instruction, indicated by line 294, the selected test is carried out. For a photometric determination, appropriate chemicals are typically added to a sample, and after an appropriate period of time, raw data, for example, percent transmission, is obtained, as indicated by "RAW DATA" box 296. As depicted by box 208 of FIG. 15, time/data data may be advantageously stored in database 30, and a test history file may be updated with time/date data when, for example, a test is begun.

As previously described, when sensing device 12 is a hand held device, manual function input 22 may be convenient for initiating countdown timing of tests. Likewise, display/input 24 may be convenient for displaying counting timing so that, for example, if an analysis involves dipping a test strip in a sample, a user is informed when to withdraw the test strip from the sample.

As depicted by line 298, raw data may be advantageously stored in database 30. Furthermore, as depicted by box 210 of FIG. 15, a test history file may be updated with raw data.

It will be readily apparent that changes can be made in the order of the steps depicted by the flow diagram of FIGS. 2 and 3. Thus, by way of illustration, an image of identifying product data could be captured or identifying product data could be manually inputted at an earlier step in the flow diagram, for example, immediately after "IS TEST AVAILABLE?" decision box 140. Similarly, the "PAIR DEVICES" step could precede the "SELECT TEST" step. Furthermore, some of the illustrated steps may be omitted. For example, an analysis may not involve a "COLLECT SAMPLE" step or a "ZERO SAMPLE" step.

Thereafter, with continued reference to FIG. 3, and with reference also to FIG. 1, raw data is beneficially communicated from sensing device 12 to device 14 via paired transceivers 16,26, and as depicted by "EXECUTE SELECTED TEST ALGORITHM" box 302, the selected test parameter algorithm is used by processor 28 to convert raw data to the test result, as illustrated by line 303 and "CONVERTED DATA" box 304.

With continued reference to FIG. 3, as depicted by line 306, converted data may be advantageously stored in database 30, and as depicted by box 212 of FIG. 15, a test history file may be updated with the converted data. As depicted by a line 308, test result data may be displayed by display 34. However, as previously indicated, when sensing device 12 is a hand held device, display 24 may be convenient for displaying test result data.

Referring again to the illustrative diagram of FIG. 15, database 30 advantageously includes a plurality of customer/ location test history files. When "INPUT CONTACT OR CURRENT LOCATION DATA" is selected, as depicted by box 202, an existing test history file may be selected, or a new test history file may be created and assigned a unique record number. By thereafter selecting "SELECT CONTACT" (see FIG. 5) customer data may be entered in the file. Alternatively, by selecting "GPS" (see FIG. 5) when device 14 includes a GPS device, the current location is entered in the file. The file may thereby be associated with a customer or location.

Using GPS or other location services as described, a user may, for example, select a particular location of a water source for analysis, and thereafter, as described hereinafter in more detail, upload test data to data repositories in cloud 50, such as a crowd sourcing data repository. In this way, a number of different users may cooperate to provide a particular crowd sourcing data repository, with significant analysis data relating to different locations of a particular water source.

Referring again to FIG. 15, a test history file may, as depicted by box 204, be updated with the selected test when "SELECT TEST" (see FIG. 3) is selected, and may, as depicted by box 206, be further updated with identifying product data in response to a "yes" output from "IS LOT NUMBER ASSOCIATED WITH ALGORITHM?" decision box (see FIG. 3). The test history file may, as depicted by box 208, be updated with time/date data when "RUN TEST" (see FIG. 3) is selected, may, as depicted by box 210, be further updated with raw test data when "RAW DATA" (see FIG. 3) is selected, and may, as depicted by box 212, be further updated with converted test data when "CONVERTED DATA" (see FIG. 3) is selected. Other updates and additions may be made to a test history file/record, as appropriate or desired.

With reference again to FIG. 3, selecting "DELETE RESULT", indicated by lines 310, 312, 314, conveniently results in display of "CONFIRM DELETE?" decision box 316. A "yes" response to "CONFIRM DELETE?" conveniently results in display of "RESULT DELETED", indicated by line 318, which, as depicted by lines 319, 320, may be accompanied by deletion of the raw data and converted data from the relevant test history file in database 30, and thereafter, as depicted by lines 319, 322, a "COLLECT SAMPLE" instruction may conveniently be displayed.

Retrieve, View And Output Data

A "no" response to "CONFIRM DELETE?" may conveniently result in display of test result data again by display 34. With continued reference to FIG. 3, selecting "EXTERNAL OUTPUT", indicated by line 330 conveniently may result in display of "OUTPUT DATA?" decision box 332. A "no" response to "OUTPUT DATA?" conveniently, as indicated by line 333, may result in display of test result data again.

With continued reference to FIG. 3, a "yes" response to "OUTPUT DATA?" results in display of a menu of external output options that, as depicted by lines 338, 340, 342, 344 and 346, may include "PRINT RESULTS", indicated by line 350, "STORE DATA", indicated by line 352, and "SHARE DATA", indicated by lines 354,356.

As indicated by line 378, selection of "PRINT RESULTS" conveniently sends data to a PRINTER 370. The printer may be used to print test results and other pertinent analysis information. As indicated by line 372, selection of "STORE DATA" may conveniently communicate data via transceiver 36 of device 14 to secure data repositories in cloud 50 for uses including back up, management and data analysis. As indicated by line 374, selection of "SHARE DATA" may communicate data via transceiver 36, for example, to social media and crowd sourcing data repositories in cloud 50. As indicated by line 376, data may also be shared via external weblinks, email and SMS, indicated by box 380. In addition, communication between device 14 and one or more other interactive visual display devices at other locations may be via cloud 50.

Figure 16:
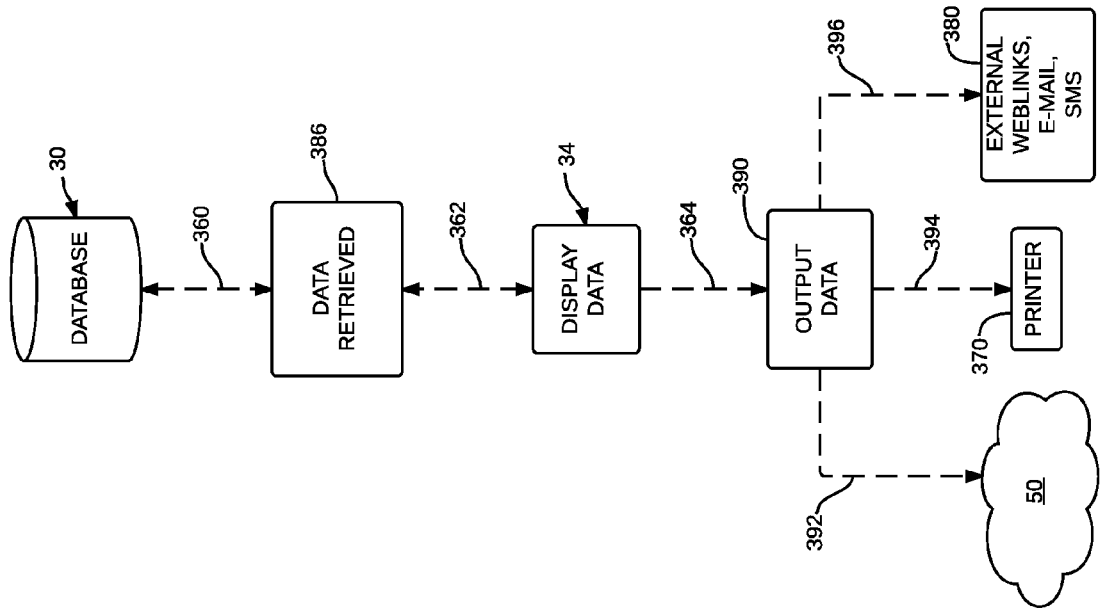
FIGS. 15 and 16 are schematic diagrams respectively illustrating input of data into a database, and retrieval, display and output of data from a database.

Referring now to FIG. 16, beginning, by way of example, with a menu of available data displayed by display 34, a user may select data for retrieval, viewing and output. As depicted by line 360 and "DATA RETRIEVED" box 386 and line 362, selected data may be retrieved and displayed. Thereafter, as depicted by line 364 and "OUTPUT DATA" box 390, and lines 392, 394, 396, selected data may be communicated to cloud 50 or to printer 370, or via external weblinks, email or text messaging, indicated by box 380.

Processor-based analysis system 10 may include additional interactive visual display devices. In such case, people may be in more than one area, and one or more additional interactive visual display devices may be located in each area. Communication between device 14 and one or more other interactive visual display devices at other locations may, for example, be via data repositories in cloud 50.

As mentioned, FIG. 2 is a simplified flow diagram, and additions and changes not shown or described can be readily appreciated. For example, in the case of multiple users of interactive visual display devices, managers can set tasks for service technicians in the field. Also by way of illustration, users may access technical information and assistance using offsite interactive question-and-answer computer resources.

Furthermore, as previously illustrated, changes can be made in the order of steps. Thus, FIG. 2 is merely illustrative of a useful flow diagram for updating a water analysis computer program, which may be an app for a smart device, and updating test algorithms, for customizing the water analysis program, for comparing identifying product data associated with an auxiliary product with identifying product data associated with a selected test parameter algorithm and determining whether the auxiliary product may be used with an intended test, and for communicating data to data repositories for purposes including storage, management, data analysis, and sharing of data.

Information may be arranged in other ways in database 30. In addition, a customer/location test history file may lack identifying product data or other data illustrated by FIG. 15. Regardless how database 30 is constructed, for a simple test history file, the test selected, time/date data, and test result may be sufficient. However, as previously described, when the inventive processor-based analysis system and method include an auxiliary product, a test history file beneficially includes identifying product data.

Referring again to FIG. 8, as depicted by an illustrative display on a "HOME" page of menu choices such as "TESTS", indicated by line 94, "HISTORY", indicated by line 95, "CALENDAR", indicated by line 96, "CUSTOMER", indicated by line 97, and "STORE", indicated by line 98, database 30 may advantageously include in addition to "HISTORY" files, other files such as "CUSTOMER" files and "CALENDAR" files.

When a water analysis program (or app) is first opened by a user, it may allow a user to respond to the query "Are you a home user?". If a user responds "yes", then the program may display the menu choice "LOCATIONS" (not shown); whereas, if a user responds "no", then the program may display the menu choice "CUSTOMERS", as illustrated by FIG. 8.

With continued reference to FIG. 8, to view prior test results, a home user may select "HISTORY", indicated by line 95. By choosing "LOCATIONS" (not shown), a home user may thereafter select from menu choices (not shown) such as "POOL", "SPA", "WELL", "POND", "AQUARIUM", and "HOUSE WATER". By choosing "STORE", indicated by line 98, a home user may select from "ADD TESTS" and "PURCHASE SUPPLIES" (not shown). By choosing "CALENDAR", indicated by line 96, a home user may be provided menu choices to create an event, specify what location to test, what water parameter(s) to test, the time and date for the test, and an alert message to alert a user to carry out the testing.

If a user is not a home user, a user may be a mobile service technician or a store service technician. In this case, a user may access a customer's history by selecting "CUSTOMERS" and then selecting the appropriate customer history record, or may select "HISTORY", which may include history for all customers, and search the "HISTORY" database for the specific customer. Like a home user, other users may select from menu choices such as "LOCATIONS", "STORE" and "CALENDAR". Other users have been previously mentioned, and can customize the inventive analysis system and method to suit their requirements.

Various modifications and combinations have been described. The present invention may be carried out with other modifications and/or combinations without departing from the spirit or essential attributes thereof. Accordingly, reference should be made to the appended claims as indicating the scope of the invention.

The invention claimed is:

1. A user-controlled, water analysis system comprising:
a sensing device comprising a colorimetric sensor capable of obtaining data for a plurality of water analysis parameters, and sensing device processing means in electronic communication with said sensor;
a mobile, user-interactive visual display device comprising user-interactive visual display means and comprising processing means in electronic communication with said visual display means, wherein said mobile, user-interactive visual display device is GPS-enabled and is at the same location as said sensing device, and is in two-way data communication with said sensing device wherein the two-way data communication is wireless and operates using a radio frequency between 2.4000 and 2.4835 Ghz, and comprises communication of water analysis data from said sensing device for processing;
an auxiliary chemical product appropriate for analysis of a user-selected water analysis parameter; and
a water analysis computer program running on the interactive visual display device processing means; said interactive visual display device processing means being in communication with a database comprising a set of executable test parameter algorithms for converting water analysis data to test result data and from which an available test parameter algorithm is selectable;
wherein a selected test parameter algorithm is executed by said processing means of said mobile, user-interactive visual display device to obtain test result data;
wherein said mobile, user-interactive visual display device further comprises communication means capable of data communication with cloud-based, data resources, and wherein the water analysis computer program and the executable test parameter algorithms are updatable by said communication means capable of said data communication; and
wherein said set of test parameter algorithms is stored on said mobile, user-interactive visual display device or stored in said cloud-based, data resources.

2. The water analysis system of claim 1, wherein said database comprises a test parameter algorithm library that comprises said set of test parameter algorithms, and in addition a plurality of unavailable test parameter algorithms available for purchase, and said test parameter algorithm library is customizable, and further comprises a selectable otherwise unavailable test parameter algorithm purchased from said plurality of unavailable test parameter algorithms, and said test parameter algorithm library is stored on said mobile, user-interactive visual display device or stored in said cloud-based, data resources.

3. The water analysis system of claim 1, further comprising a test parameter algorithm store accessible by said communication means capable of said data communication, wherein said test parameter algorithm store comprises a plurality of test parameter algorithms available for purchase, and wherein a test parameter algorithm library comprises said set of test parameter algorithms, and a selectable otherwise unavailable test parameter algorithm purchased from said store.

4. The water analysis system of claim 1, wherein a test parameter algorithm library comprises said set of test parameter algorithms, and said set of test parameter algorithms includes an updated test parameter algorithm, and wherein the selected test parameter algorithm is an updated test parameter algorithm associated with identifying product data capable of being compared with identifying product data of said auxiliary chemical product, and said user-interactive visual display means of said mobile, user-interactive visual display device displays alerts comprising a notification to update one or more test parameter algorithms in said test parameter algorithm library.

5. The water analysis system of claim 1, wherein said auxiliary chemical product is associated with identifying product data, and said selected test parameter algorithm is associated with identifying product data capable of being compared with said identifying product data of said auxiliary chemical product.

6. The water analysis system of claim 5, wherein said mobile, user-interactive visual display device further comprises image capture means.

7. The water analysis system of claim 6, wherein encoded identifying product data associated with said auxiliary chemical product, is captured by said image capture means, and wherein data comprising said encoded identifying product data and said test result data is stored in said database, and said test result data is associated with the encoded identifying product data associated with said auxiliary chemical product.

8. The water analysis system of claim 1, wherein said sensing device is a hand-held instrument and further comprises temperature sensing means, and said set of test parameter algorithms are temperature variable.

9. The water analysis system of claim 1, wherein said mobile, user-interactive visual display device further comprises time/date means in electronic communication with said interactive visual display device processing means for associating test data with location and time/date data.

10. The water analysis system of claim 1, wherein said cloud-based, data resources comprise (i) data repositories for sharing data, and said data repositories for sharing data comprise social media data repositories and crowd sourcing data repositories, or (ii) data repositories for storage, management and/or analysis of data.

11. The water analysis system of claim 1, wherein said database is in a secure data repository in said cloud-based data resources or stored on said mobile, user-interactive visual display device.

12. The water analysis system of claim 1, wherein said sensing device further comprises (a) means for manually operating said sensing device, and (b) visual display means in electronic communication with the sensing device processing means.

13. The water analysis system of claim 1, wherein a water-based liquid is analyzed for said user-selected water analysis parameter, and wherein said sensing device is configured to hold a sample being analyzed.

14. The water analysis system of claim 1, wherein said set of test parameter algorithms is stored on said mobile, user-interactive visual display device.

15. The water analysis system of claim 1, wherein the data communication further comprises communication of the user-selected analysis parameter from the mobile, user-interactive visual display device to said sensing device.

16. The water analysis system of claim 1, wherein said mobile, user-interactive visual display device is a smart device and said water analysis computer program is an app for a smart device, and the location of said sensing device and said mobile, user-interactive visual display device is a sampling site, and the two-way wireless communication is at the sampling site.

17. A user-controlled, water analysis method comprising: running a water analysis computer program on a mobile, user-interactive visual display device comprising processing means, communicating a user-selected water parameter from said mobile, user-interactive visual display device to a sensing device comprising processing means and a colorimetric sensor capable of obtaining data for a plurality of water parameters, adding an auxiliary chemical product appropriate for analyzing the user-selected water parameter to a water sample, obtaining data for the user-selected water parameter and communicating the analysis data from said sensing device to said mobile, user-interactive visual display device, and processing the analysis data to obtain test result data,
wherein the mobile, user-interactive visual display device is GPS-enabled and is in wireless communication with, and located together with, said sensing device for said communicating, wherein said wireless communication operates using a radio frequency between 2.4000 and 2.4835 Ghz, and
wherein a set of test parameter algorithms for converting said analysis data to said test result data is stored on said mobile, user-interactive visual display device or stored in cloud-based, data resources, and wherein said method further comprises one or both of
(i) updating a test parameter algorithm by data communication with cloud-based, data resources, selecting the updated test parameter algorithm from said set of test parameter algorithms, and executing said selected test parameter algorithm to process said analysis data, or
(ii) customizing a test parameter algorithm library by purchase of an otherwise unavailable test parameter algorithm, selecting a test parameter algorithm from available test parameter algorithms in the customized algorithm library, and executing said selected test parameter algorithm to process said analysis data.

18. The analysis method of claim 17, further comprising, prior to the addition of said auxiliary chemical product, comparing identifying product data associated with said auxiliary chemical product with identifying product data associated with said selected test parameter algorithm.

19. The method of claim 18, further comprising prior to said comparing, capturing said identifying product data associated with said auxiliary chemical product, by use of image capture means, wherein said identifying product data is encoded identifying product data, and said mobile, user-interactive visual display device comprises said image capture means.

20. The method of claim 18, further comprising validating use of said auxiliary chemical product for analysis of said selected water parameter, by said comparing.

21. The method of claim 17, wherein said sensing device is contacted by a user with water being analyzed and thereafter withdrawn from contact with water being analyzed, prior to the addition of said auxiliary chemical product, and the mobile, user-interactive visual display device and said sensing device are located together at a sampling site for the water analysis.

22. The method of claim 17, wherein said test parameter algorithm is updated by updating said computer program.

23. The method of claim 17, wherein said test parameter algorithm library further comprises a plurality of unavailable test parameter algorithms available for purchase.

24. The method of claim 17, wherein said purchase of an otherwise unavailable test parameter algorithm is from a test parameter algorithm store accessible by communication means of said mobile, user-interactive visual display device capable of data communication with cloud-based, data resources.

25. A user-controlled, water analysis system comprising:
a hand-held sensing device comprising a sensor capable of obtaining data for a plurality of water analysis parameters, and sensing device processing means in electronic communication with said sensor, wherein said hand-held sensing device is a hand-held photometer;
a mobile, user-interactive visual display device comprising user-interactive visual display means and comprising processing means in electronic communication with said user-interactive visual display means, wherein said mobile, user-interactive visual display device is a smart device further comprising image capture means, and is GPS-enabled and is at the same location as said hand-held photometer, and is in two-way data communication with said hand-held photometer wherein the two-way data communication is wireless and operates using a radio frequency between 2.4000 and 2.4835 Ghz and comprises communication of a user-selected water analysis parameter from said smart device to said hand-held photometer, and of water analysis data from said hand-held photometer to said smart device for processing;
an auxiliary chemical product appropriate for analysis of a user-selected water analysis parameter, and
a water analysis computer program running on the smart device processing means; said smart device processing means being in communication with a database comprising a test parameter algorithm library comprising a set of executable test parameter algorithms for converting water analysis data to test result data and from which an available test parameter algorithm is selectable, wherein said test parameter algorithm library further comprises a plurality of unavailable test parameter algorithms available for purchase;

wherein a selected test parameter algorithm is executed by said smart device processing means to obtain test result data;

wherein said smart device further comprises communication means capable of data communication with cloud-based, data resources, and wherein the water analysis computer program and the executable test parameter algorithms are updatable by said communication means capable of said data communication; and wherein said set of test parameter algorithms is stored on said smart device or stored in said cloud-based, data resources.

\* \* \* \* \*